(12) United States Patent
Margiotta et al.

(10) Patent No.: US 12,324,486 B2
(45) Date of Patent: Jun. 10, 2025

(54) INSOLE APPARATUS AND METHOD OF MANUFACTURE THEREOF

(71) Applicant: TYFO SPORTS LIMITED, Letterkenny (IE)

(72) Inventors: Ezio Margiotta, Letterkenny (IE); Siimon Skirrow, Letterkenny (IE)

(73) Assignee: TYFO SPORTS LIMITED, Letterkenny (IE)

( * ) Notice: Subject to any disclaimer, the term of this patent is extended or adjusted under 35 U.S.C. 154(b) by 608 days.

(21) Appl. No.: 17/310,177

(22) PCT Filed: Jan. 24, 2020

(86) PCT No.: PCT/EP2020/051719
§ 371 (c)(1),
(2) Date: Jul. 23, 2021

(87) PCT Pub. No.: WO2020/152313
PCT Pub. Date: Jul. 30, 2020

(65) Prior Publication Data
US 2022/0117353 A1    Apr. 21, 2022

(30) Foreign Application Priority Data
Jan. 24, 2019 (GB) ..................... 1900971

(51) Int. Cl.
*A43B 7/1425* (2022.01)
*A43B 7/144* (2022.01)
(Continued)

(52) U.S. Cl.
CPC ............ *A43B 7/1425* (2013.01); *A43B 7/144* (2013.01); *A43B 7/1445* (2013.01); *A43B 17/00* (2013.01)

(58) Field of Classification Search
CPC ..... A43B 7/144; A43B 7/1445; A43B 7/1425; A43B 17/00
See application file for complete search history.

(56) References Cited

U.S. PATENT DOCUMENTS 1,518,840 A * 12/1924 De Ridder ........... A43B 7/1425
                                                              12/21
1,702,531 A *  2/1929 Ambill ................ A43B 1/0045
                                                              36/146
(Continued)

FOREIGN PATENT DOCUMENTS

GB       2358121 A     7/2001
WO    2009026492 A1    2/2009

OTHER PUBLICATIONS

International Bureau in connection with PCT/EP2020/051719 filed Jan. 24, 2020, "International Preliminary Report on Patentability", 7 pages, mailed Aug. 5, 2021.
(Continued)

*Primary Examiner* — Heather Mangine
*Assistant Examiner* — Raquel M. Weis
(74) *Attorney, Agent, or Firm* — McKee, Voorhees Sease, PLC

(57) ABSTRACT

The invention provides an insole apparatus for use with an item of footwear. The insole includes upper and opposing lower faces, the upper face being arranged to interface with the sole of a user's foot, in use. The upper face includes two or more areas or regions wherein a portion or portions of the surface of the upper face is raised relative to the remainder of the upper face, the areas or regions positioned to target at least two regions of cutaneous mechanoreceptors in the user's foot, in use. Also provided is an item of footwear including an insole apparatus as herein defined.

9 Claims, 5 Drawing Sheets

Figure 1H:
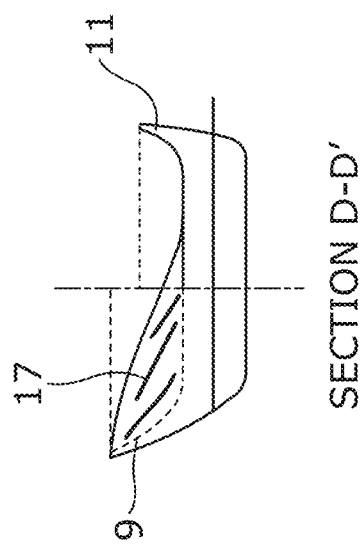
Figure 1G:
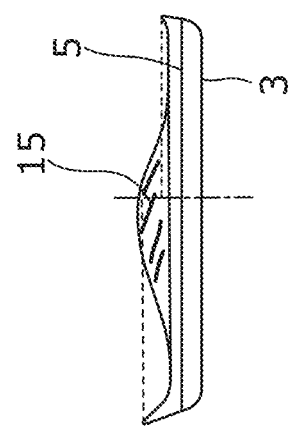
Figure 1F:
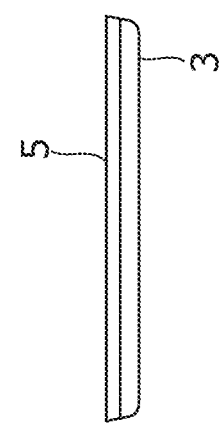
Figure 2F:
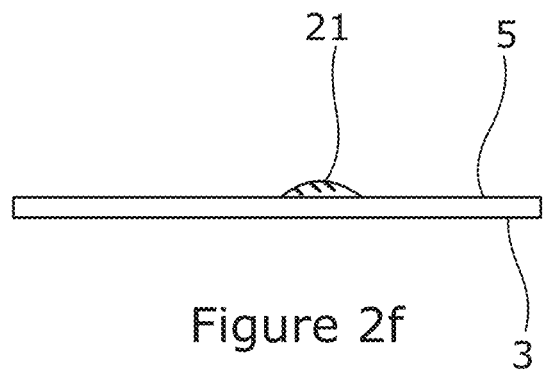
Figure 2G:
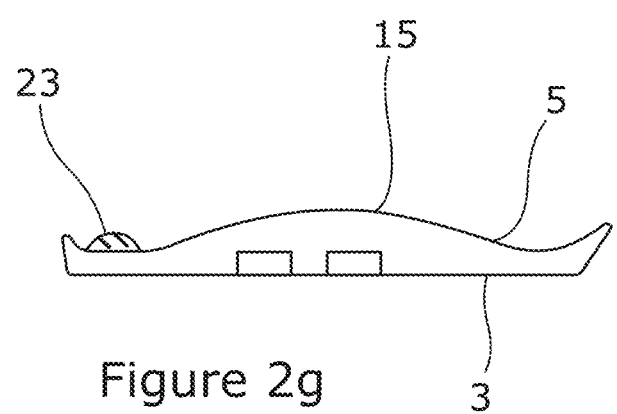
Figure 2H:
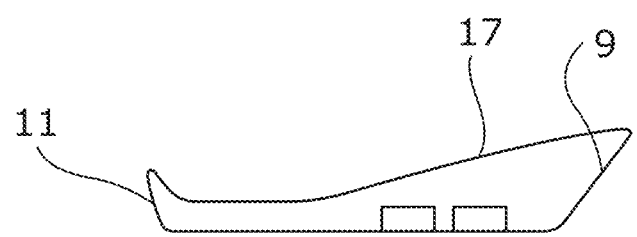
Figure 2I:

(51) Int. Cl.
*A43B 7/1445* (2022.01)
*A43B 17/00* (2006.01)

(56) References Cited

U.S. PATENT DOCUMENTS

| | | | | |
|---|---|---|---|---|
| 1,850,122 A * | 3/1932 | Thomas | A43B 7/1445 | 36/159 |
| 1,916,198 A * | 7/1933 | Musebeck | A43B 7/142 | 36/22 A |
| 2,008,985 A * | 7/1935 | Lattemann | A43B 7/1435 | 36/145 |
| 4,020,570 A * | 5/1977 | Shames | A43B 17/14 | 36/44 |
| 4,033,054 A * | 7/1977 | Fukuoka | A43B 7/146 | 601/134 |
| 4,841,647 A * | 6/1989 | Turucz | A43B 7/146 | 36/43 |
| 5,322,056 A * | 6/1994 | Menghi | A43B 13/40 | 601/134 |
| 5,551,173 A * | 9/1996 | Chambers | A43B 7/149 | 36/141 |
| 5,685,094 A * | 11/1997 | Lin | A43B 1/0054 | 36/43 |
| 5,787,608 A * | 8/1998 | Greenawalt | A61F 5/14 | 36/169 |
| 5,860,229 A * | 1/1999 | Morgenstern | A43B 7/1415 | 36/141 |
| 5,976,100 A * | 11/1999 | Greenawalt | A43B 7/142 | 36/43 |
| 6,082,024 A * | 7/2000 | Del Biondi | A43B 13/14 | 601/134 |
| 6,131,311 A * | 10/2000 | Brown | A43B 7/142 | 36/43 |
| 6,510,626 B1 * | 1/2003 | Greenawalt | A43B 7/142 | 36/43 |
| 6,732,457 B2 * | 5/2004 | Gardiner | A43B 13/38 | 36/43 |
| 6,742,289 B2 * | 6/2004 | Celmo | A43D 999/00 | 36/43 |
| 7,426,794 B2 * | 9/2008 | Swensen | A43B 7/1464 | 36/43 |
| 7,980,008 B2 * | 7/2011 | Song | A43B 21/28 | 36/27 |
| 8,745,894 B2 * | 6/2014 | Cheskin | A43B 17/08 | 36/3 R |
| 9,943,132 B1 * | 4/2018 | Tsai | A43B 17/006 | |
| 2013/0160331 A1 * | 6/2013 | Burke | A43B 7/144 | 36/43 |
| 2015/0272273 A1 | 10/2015 | Whittingham | | |

OTHER PUBLICATIONS

International Searching Authority in connection with PCT/EP2020/051719 filed Jan. 24, 2020, "Written Opinion of the International Searching Authority", 5 pages, mailed Aug. 5, 2021.
ESPACENET Abstract of GB2358121, accessed on Aug. 20, 2021.

* cited by examiner

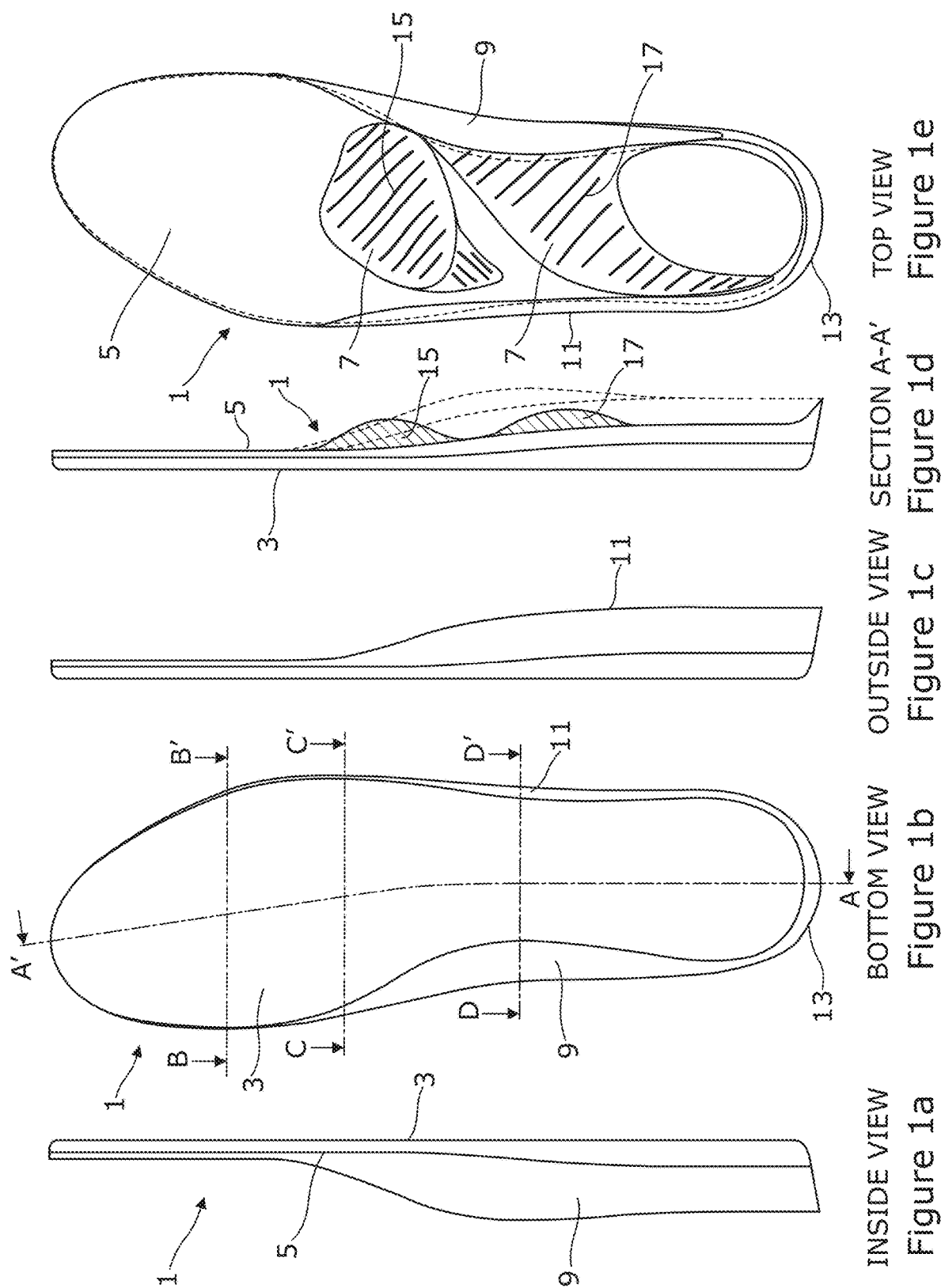

SECTION D-D'

SECTION C-C'

SECTION B-B'

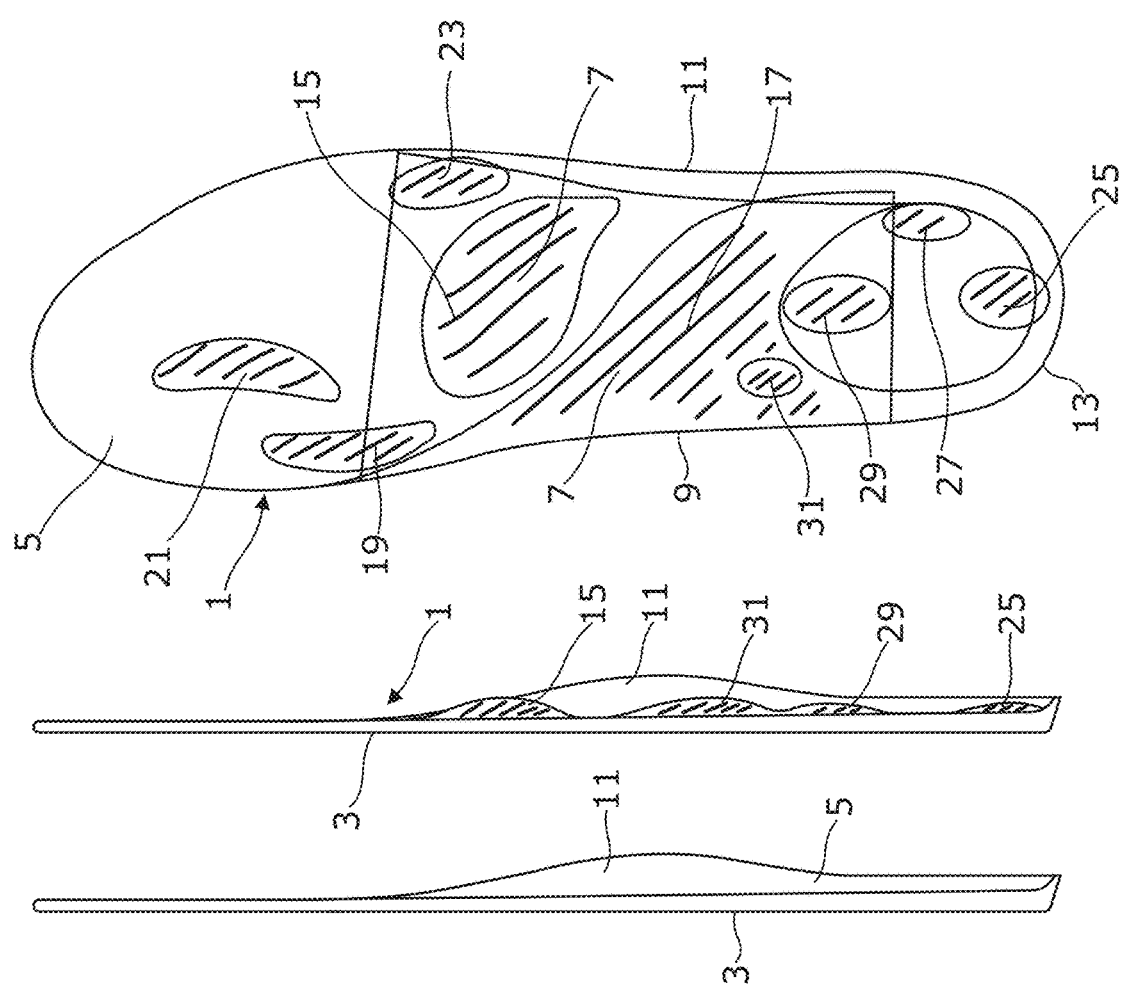
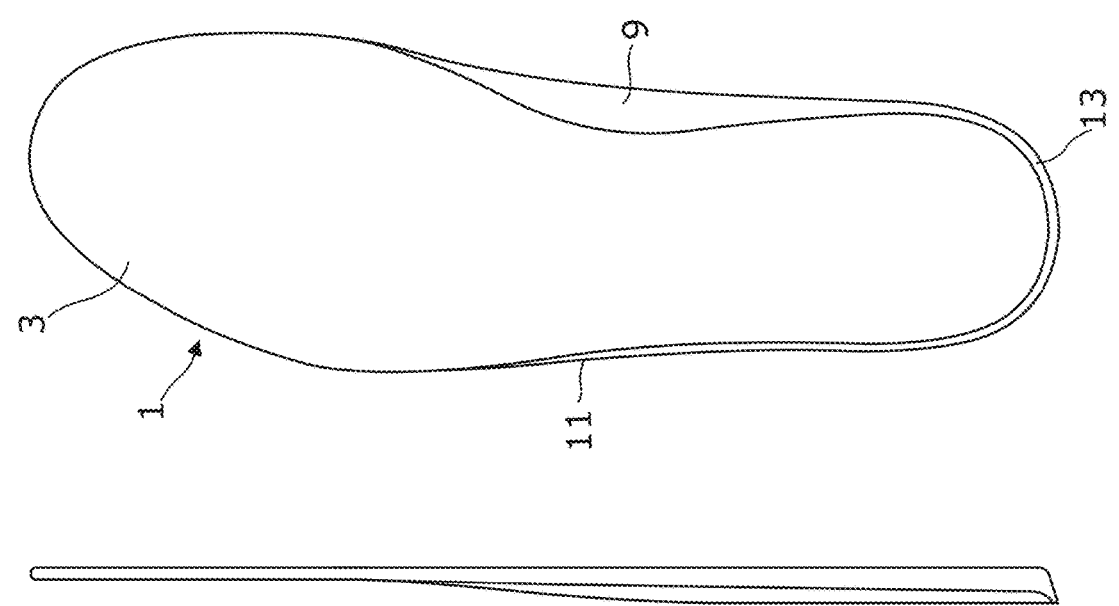
Figure 2a   Figure 2b   Figure 2c   Figure 2d   Figure 2e

INSOLE APPARATUS AND METHOD OF MANUFACTURE THEREOF

CROSS REFERENCE TO RELATED APPLICATIONS

This is a U.S. national phase application claiming priority to PCT/EP2020/051719, filed Jan. 24, 2020, which claims priority to British application No. 1900971.1, filed Jan. 24, 2019, the entire contents of each of which are hereby incorporated by reference in their entireties.

The invention to which this application relates is an insole apparatus for use with an item of footwear, and a method of manufacture thereof.

Shoe inserts, more formally known as foot orthoses, are used for several reasons such as comfort, pain relief, injury rehabilitation, cushioning or massaging joints ad structures of the foot, orthopaedic correction and athletic performance. These are usually provided as insertable insoles for an item of footwear. Insoles are generally provided in one of two forms: those that uniformly distribute any texture and/or contours or structural topography of the footbed across entire foot-footbed interface, however this in effect impairs the discriminatory sensory input to proprioceptive engagement and higher centres; and those insoles which have a focus on rehabilitation of the medial arch. However, at best, medial arch devices can influence only up to 10%-30% of the gait cycle through the mid-stance phase of any single leg support. Therefore, any activities where the heel and forefoot ground contact are critical cannot be engaged optimally through purely arch constructed devices; they do not recognise the plantar foot as a major sensory organ via glabrous skin. An example of such an insole may be seen in U.S. Pat. No. 6,301,807, which discloses an insole designed to promote proprioceptive stimulation of the golgi tendon organ. While the disclosed insole provides support for a user's medial arch, and aims to stimulate the golgi tendon organ, the insole ultimately only targets one of at least eight somatic sensory nerve ending present in the foot—the golgi tendon organ. Insoles which are currently available, therefore, only target small or singular regions of the foot, and thus do not offer adequate stimulation for all groups of cutaneous mechanoreceptors across the foot.

It is therefore an aim of the present invention to provide an improved insole apparatus that overcomes the problems associated with the prior art.

It is a further aim of the present invention to provide an item of footwear including an improved insole apparatus that overcomes the problems associated with the prior art.

It is a further aim of the present invention to provide a method of manufacturing an improved insole apparatus that overcomes the problems associated with the prior art.

It is a further aim of the present invention to provide a method of manufacturing an item of footwear including an improved insole apparatus that overcomes the problems associated with the prior art.

According to a first aspect of the invention there is provided an insole apparatus for use with an item of footwear, said insole apparatus including:
  upper and opposing lower faces, said upper face arranged to interface with the sole of a user's foot, in use;
  characterized in that said upper face includes two or more areas or regions wherein a portion or portions of the surface of the upper face is raised relative to the remainder of the upper face, said areas or regions positioned to target at least two regions of cutaneous mechanoreceptors in the user's foot, in use.

In one embodiment, said portion or portions may include any or any combination of a plurality of formations, projections and/or nodes, or a single-shaped raised portion or formation across the given area or region of the upper face.

In one embodiment, the insole apparatus is formed to target the cutaneous and musculoskeletal proprioceptive mechanoreceptors in the sole of a user's foot, in use, which have been shown to influence leg muscle motor neurons. Typically, said two or more areas or regions wherein a portion or portions of the surface of the upper face is raised relative to the remainder of the upper face are provided to target the cutaneous and musculoskeletal proprioceptive mechanoreceptors in the sole of a user's foot, in use, which have been shown to influence leg muscle motor neurons.

Preferably, said raised portions, projections, formations and/or nodes are formed to mirror major sensitive regions of a user's plantar foot, in use. Typically, said regions include any or any combination of: the medial longitudinal arch, lateral longitudinal arch, anterior transverse arch, heel, fifth metatarsal and toe and/or first metatarsal and toe.

In one embodiment, a first of said two or more areas or regions includes the central forefoot. Typically, there is provided a raised portion or formation in the area or region of the upper face which targets or mirrors the central forefoot of a user, in use. Further typically, said raised portion has a maximum height at its apex, relative to the remainder of the upper face, of between 8 to 30 mm.

In one embodiment, said raised portion may extend from the proximal one third of the first metatarsal shaft base to one third of the fourth metatarsal shaft base.

In one embodiment, a second of said two or more areas or regions includes the medial midfoot region. Typically, there is provided a raised portion or formation in the area or region of the upper face which targets or mirrors the medial midfoot region of a user, in use. Further typically, said raised portion or formation has a maximum height, relative to the remainder of the upper face, of between 12 to 40 mm.

In one embodiment, said second raised portion or formation located in the region from where the medial longitudinal arch borders, from the heel region of the insole apparatus to a point mirroring the base of the first metatarsal phalangeal joint of a user, in use.

In one embodiment, one or more further portions or nodes may be provided, said portions or nodes being located on the upper face of said insole apparatus to mirror or target any or any combination of: medially at the base of the first metatarsal phalangeal joint; the base of the first interphalangeal joint closest to midline, extending to the base of the second metatarsal phalangeal joint; the proximal base fifth metatarsal phalangeal joint; the central heel pad at the midline maximally posterior; at the heel pad at 50% heel length maximally laterally; the midline proximal limit heel pad; and medially on a secondary medial midfoot portion or formation, where provided.

In a preferred embodiment of the invention, further portions or nodes may be provided, said portions or nodes being located on the upper face of said insole apparatus to mirror or target: medially at the base of the first metatarsal phalangeal joint; the base of the first interphalangeal joint closest to midline, extending to the base of the second metatarsal phalangeal joint; the proximal base fifth metatarsal phalangeal joint; the central heel pad at the midline maximally posterior; at the heel pad at 50% heel length maximally laterally; and the midline proximal limit heel pad.

In one embodiment, each of said one or more further portions or nodes may have a height: base ratio of 1:10.

However, the skilled person will appreciate that this may be varied depending on the foot size and shape, and overall size/weight of the user. As such, the densities may also be varied accordingly in order to maximise the desired feeling of mechanoreceptor stimulation, in use.

In one embodiment, said insole apparatus includes a first raised portion or formation in the area or region of the upper face which targets or mirrors the central forefoot of a user, in use, a second raised portion or formation in the area or region of the upper face which targets or mirrors the medial midfoot region of a user, in use, and a plurality of further raised portions or nodes, located on the upper face of said insole apparatus to mirror or target any or any combination of: medially at the base of the first metatarsal phalangeal joint; the base of the first interphalangeal joint closest to midline, extending to the base of the second metatarsal phalangeal joint; the proximal base fifth metatarsal phalangeal joint; the central heel pad at the midline maximally posterior; at the heel pad at 50% heel length maximally laterally; the midline proximal limit heel pad; and medially on the medial midfoot portion or formation. In one embodiment, at least one raised portion is provided to target each of said areas or regions.

In one embodiment, a plurality of dimples or formations are provided on the upper face, across at least a part of remaining regions where there are no raised portions, projections or nodes. Typically, said dimples or formations are provided smaller in size than the said raised portions, projections or nodes. Typically, said dimples or formations are formed/provided on said surface in a non-uniform or irregular manner. Preferably, said dimples or formations may be provided in one or more selected remaining regions of the upper face of the insole.

In another embodiment, a plurality of dimples or formations may be provided on at least a part of the surface of the raised portions, projections or nodes. Typically, said dimples or formations are provided smaller in size than the said raised portions, projections or nodes. Typically, said dimples or formations are formed/provided on said surface in a non-uniform or irregular manner. Preferably, said dimples or formations may be provided in one or more selected regions on the surface of selected portions, projections or nodes.

Thus, the provision of additional dimples or formations may serve to further stimulate the mechanoreceptors in the sole of a user's foot, in use.

Embodiments of the present invention therefore serve to target all fast adapting (FAI, FAII) and slow adapting (SAI, SAII) cutaneous mechanoreceptors in a user's foot, in use, which provide input to the central nervous system for a more complete picture to the nervous system higher centres processing sensory information. This results in increased stimulation for a user right through the gait cycle.

Specific targeting such as that described above serves to provide fuller gait cycle activation for a user from the foot-footbed interface well beyond 30%, providing a very distinct advantage over that which is available in the prior art. Stimulation of the cutaneous mechanoreceptors is therefore provided by the insole apparatus of the present invention from initial heel contact, loading, mid-stance through to toe-off. The features of the present invention therefore allow for any foot activity in weight-bearing postures that emphasize the heel, toes and/or midfoot arch to be more fully stimulated, thus having broader dynamic applications, while the mechanoreceptors targeted include both fast and slow acting fibres and are sensitive to pressure, stretch, skin movement & vibration.

In one embodiment, the insole apparatus may be provided in varying thicknesses in order to accommodate users of differing body masses.

In another embodiment, the insole apparatus may be provided in materials of varying densities in order to accommodate users of differing body masses.

In one embodiment, said apparatus may be formed of a material or materials such that the density of the insole may be varied in different areas or regions of the insole. Typically, said two or more areas or regions wherein a portion of the surface of the upper face is raised relative to the remainder of the upper face may be provided of a different density to the main body of the insole apparatus.

In one embodiment, said insole apparatus is formed from a polymeric material. Preferably, said polymeric material is a lightweight polymer. Typically, said material is polyurethane. Preferably, said apparatus is formed from injection-moulded polyurethane. In other embodiments, said insole apparatus is formed from compression moulding or 3D construction, or combinations thereof.

In one embodiment, said portions, projection, formation and/or nodes may be formed having a different density to the remainder of the insole apparatus.

In one embodiment, said upper face may include a further surface layer attached, bonded and/or adhered thereto. Typically, said further surface layer may be a textured or tactile layer.

In one embodiment, said insole apparatus is adapted to be received in an item of footwear, forming at least part of a footbed thereof. Typically, said item of footwear may be a shoe, sandal, boot, sock, sports-related footwear, high-top boots, basketball shoes, ski boots and/or the like.

In one embodiment, said insole apparatus may be formed to be insertable and removable from said item of footwear. In another embodiment, said insole apparatus may be formed integrally with said item of footwear.

In one embodiment, said insole apparatus may include one or more raised side and/or rear portions, located at or along the periphery of the insole apparatus. Typically, said raised side and/or rear portions enable a user's foot to be located correctly and comfortably on the upper face of the insole apparatus, in use.

Preferably, said two or more areas or regions wherein a portion or portions of the surface of the upper face is raised relative to the remainder of the upper face, are distinct from one or more raised side and/or rear portions, located at or along the periphery of the insole apparatus. In another embodiment, at least one of said portions of the surface of the upper face, raised relative to the remainder of the upper face, may extend inwardly of the insole apparatus from a raised side wall or portion located at or along the periphery of the insole apparatus.

In another embodiment of the present invention, said insole apparatus may include one or more implants, sensors and/or other electronics items located therein. Typically, said implants and/or sensors may be provided to detect motion, activity, stimulation and/or the like of the user, in use. In other embodiments, said one or more implants, sensors and/or other electronics items may be provided to form part of, or communicate with any or any combination of integrated wearable technologies, or artificially assisted or augmented motion technologies.

Typically, said one or more one or more implants, sensors and/or other electronics items are located in each of the portions, formations, projections, nodes or domes provided in the insole apparatus.

In another aspect of the present invention, there is provided an item of footwear including an insole apparatus as described above.

In another aspect of the present invention, there is provided an item of footwear including a chassis specifically adapted to receive an insole apparatus as described above.

In one embodiment, said insole apparatus may be formed to be insertable and removable from said item of footwear. In another embodiment, said insole apparatus may be formed integrally with said item of footwear.

In another aspect of the present invention, there is provided a method of forming an insole apparatus, said method including the steps of:
  Forming a body of the insole apparatus having upper and opposing lower faces, said upper face being arranged to interface with the sole of a user's foot, in use;
  characterized by forming on said upper face two or more areas or regions wherein a portion or portions of the surface of the upper face is raised relative to the remainder of the upper face, said areas or regions being positioned to target at least two regions of cutaneous mechanoreceptors in the user's foot, in use.

In one embodiment, sad insole is subsequently inserted into an item of footwear, for subsequent use by a user. In another embodiment, said insole apparatus is formed integrally with an item of footwear.

In a further aspect of the present invention, there is provided an item of footwear including a chassis and a footbed, said footbed including:
  an upper face arranged to interface with the sole of a user's foot, in use;
  characterized by said upper face including two or more areas or regions wherein a portion or portions of the surface of the upper face is raised relative to the remainder of the upper face, said areas or regions positioned to target at least two regions of cutaneous mechanoreceptors in the user's foot, in use.

Typically, said item of footwear may be a shoe, sandal, boot, sock, sports-related footwear, high-top boots, basketball shoes, ski boots and/or the like.

In some embodiments, said item of footwear may be formed extend over the ankle of a user, in use. Typically, such an item of footwear, may include one or more further portions or nodes formed to target or mirror any or any combination of: the lateral and/or medial ankle, and/or posterior region adjacent the tendoachilles region of a user, in use.

Typically, said item of footwear may be provided as a one piece knitted, laminated, over moulded, injected &/or compression moulded item, or be formed from a combination of these techniques.

In another aspect of the present invention, there is provided an insole apparatus, said apparatus including a plurality of contours and formations and/or projections arranged to target cutaneous and musculoskeletal proprioceptive mechanoreceptors in the sole of a user's foot, in use.

Figure 3:
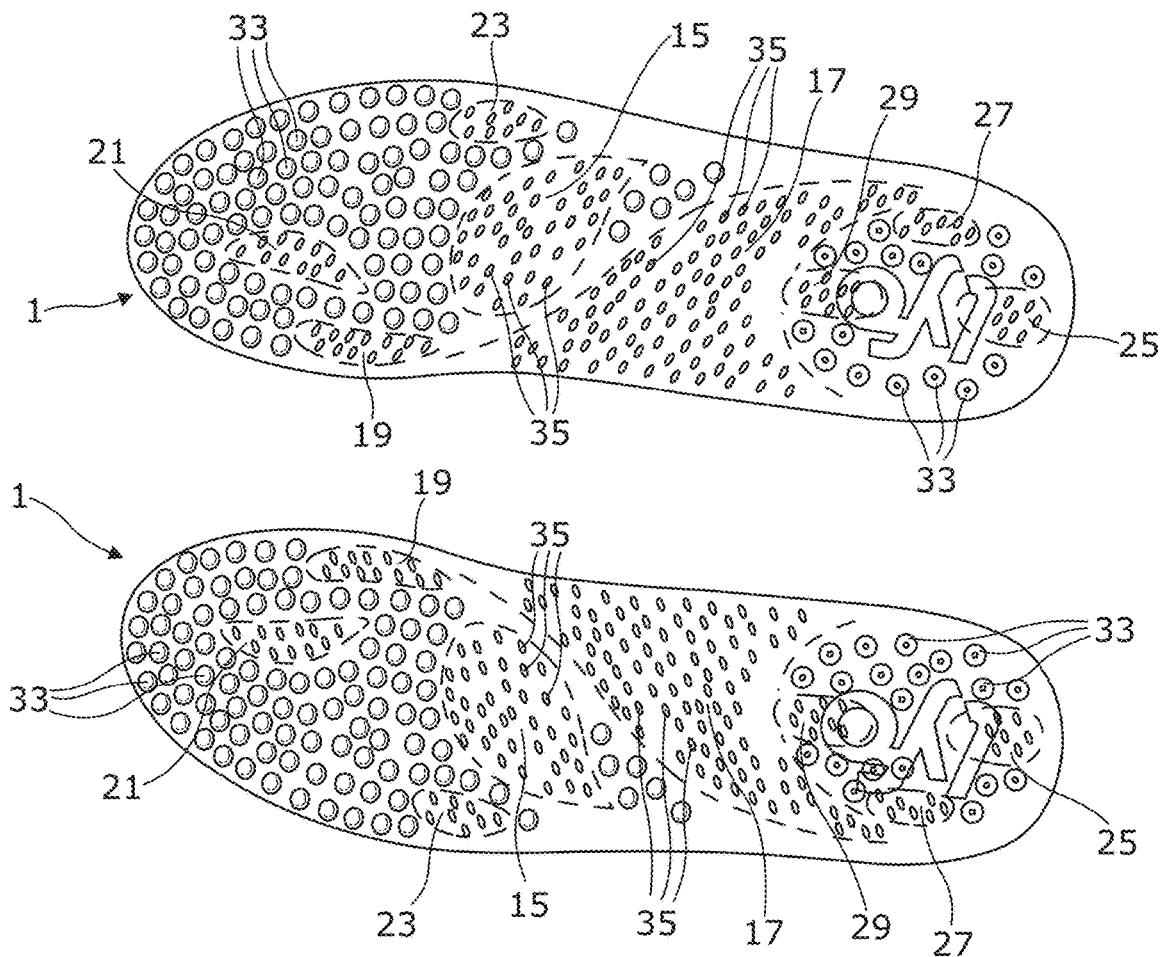
Figure 4:
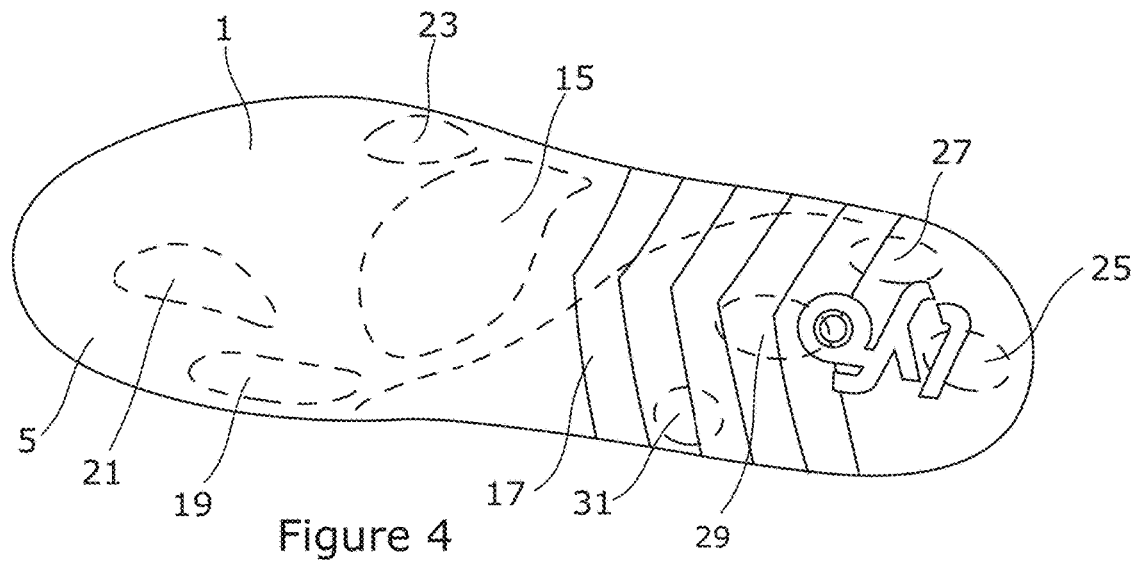

Embodiments of the present invention will now be described with reference to the accompanying figures, wherein:

FIGS. 1a-h illustrate multiple views of an insole apparatus according to an embodiment of the present invention;

FIGS. 2a-i illustrate multiple views of an insole apparatus according to another embodiment of the present invention;

FIG. 3 illustrates a top view of a pair of insole apparatus according to an embodiment of the present invention; and FIG. 4 illustrates a top view of an insole apparatus according to another embodiment of the present invention.

Referring now to the figures, there is illustrated an improved insole apparatus 1 in accordance with the present invention. The insole includes a lower face 3 and, in particular, an opposing upper face 5, on which there are provided at least two areas or regions 7 that include a portion of the upper face 5 which is raised relative to the remaining areas of the upper face 5. The areas or regions 7 in which there is a raised portion or portions are those which target at least two regions of cutaneous mechanoreceptors in a user's foot when the user is wearing footwear with the insole 1 included or inserted. The raised portions may include any or any combination of a plurality of formations, projections or nodes, or, as shown in the figures, singularly-shaped raised portions or domes across the given area or region 7 of the upper face 5. In practice, the provision of an insole 1 as described, having specific raised portions, formations, projections and/or nodes, enables the targeting of the cutaneous and musculoskeletal proprioceptive mechanoreceptors in the sole of a user's foot, in use, which have been shown to influence leg muscle motor neurons. Consequently, this serves to provide greater stimuli to a user throughout the gait cycle encouraging greater muscle activation in the user's feet.

Specifically, the present invention provides a first raised portion or dome (or plurality of projections or formations) which is formed in the area or region of the upper face which targets or mirrors the central forefoot 15 of a user, in use. Typically, this portion or dome 15 is formed having a maximum height at its apex, relative to the remainder of the upper face 5, of between 8 to 30 mm. A second raised portion or dome, according to an embodiment of the invention, may be formed in the area or region of the upper face 5 which targets the medial midfoot region 17 of a user, in use, and this raised portion or dome effectively targets the region from where the medial longitudinal arch borders, from the heel region of the insole apparatus to a point mirroring the base of the first metatarsal phalangeal joint of a user, in use. Typically, this portion or dome is formed having a maximum height, relative to the remainder of the upper face 5, of between 12 to 40 mm.

Further raised portions or nodes 19-31 which may be provided in the present invention all together or in various combinations are illustrated in particular in FIG. 2e, these being located on the upper face 5 of the insole 1 to mirror or target any or any combination of: medially at the base of the first metatarsal phalangeal joint 19; the base of the first interphalangeal joint closest to midline, extending to the base of the second metatarsal phalangeal joint 21; the proximal base fifth metatarsal phalangeal joint 23; the central heel pad at the midline maximally posterior 25; at the heel pad at 50% heel length maximally laterally 27; the midline proximal limit heel pad 29; and medially on a secondary medial midfoot portion or dome 31.

Essentially, the present invention provides an insole 1 wherein two larger portions or domes 15, 17 may be provided, together with further regions which may be served by the provision of additional tertiary projections or nodes (19-31) on the upper face 5 of the insole 1, seven of which are illustrated, to provide the desired stimulation and gait cycle activation for a user. At least two are provided in an insole 1 according to the present invention, wherein in a preferred embodiment of the invention, at least a first is located to target the central forefoot 15 of a user, with second or further portions, domes or nodes being in any or any combination of the remaining locations (17-31), depending on the specific requirements of the user.

In one specific embodiment, portions or nodes may be provided at least at each of eight specified locations (15-29).

FIG. 3 illustrates and embodiment of the present invention, wherein a pair of insoles 1 are shown. In this embodiment, eight specific regions are provided having raised portions or nodes, those being: medially at the base of the first metatarsal phalangeal joint 19; the base of the first interphalangeal joint closest to midline, extending to the base of the second metatarsal phalangeal joint 21; the proximal base fifth metatarsal phalangeal joint 23; the central heel pad at the midline maximally posterior 25; at the heel pad at 50% heel length maximally laterally 27; and the midline proximal limit heel pad 29. In addition to this, the insoles 1 of FIG. 3 further include a plurality of smaller dimples or formations 33 located across the remaining surface of the insole 1 which isn't raised or at which there is provided a raised portion or node. While FIG. 3 illustrates the dimples or formations 33 being distributed uniformly across the whole of the remaining (non-raised) surface, preferred embodiments of the invention will provide a plurality of dimples or formations 33 in a non-uniform manner across parts of the remaining surface. This can be important because it is the non-uniformity/irregularity of the dimples or formations, and the larger portions or nodes which serves to create stimuli in a user's foot. If the dimples or formations 33, for example, were spread evenly and uniformly across the whole of the insole, this essentially dilutes the desired effect and the stimulation in a user's foot is reduced. In some embodiments of the present invention, and as also illustrated in FIG. 3, the raised portions or domes (15-29) may also be provided with at least a part of their surface including a plurality of smaller dimples or formations 35. This can equally apply to insoles where portion or node 31 is also provided. Thus, the provision of a plurality of additional dimples or formations 33 and/or 35 may serve to further stimulate the mechanoreceptors in the sole of a user's foot.

FIG. 4 illustrates a further insole 1 in accordance with the invention, wherein raised portions or nodes are formed as described above, with the added inclusions of portion or node 31, but the remaining surface 5 of the insole, and also the surface of those raised portions or nodes are substantially smooth.

The improved insole 1 of the present invention essentially casts a greater 'net' through the skin & muscular mechanoreceptors; the insole 1 enables the sending of more signals due to the pressure, tension, stretch, vibration and movement stimuli that occurs naturally as the foot an leg move and come to ground, which in turn activates more motor units (motor neuron fibre & the number of muscle fibres it activates). This is due to the increased presence and specifically-located portions 7 on the insole, and which are simply not envisaged in the prior art examples. Each ground reaction force, through running, walking, jumping etc., regardless of foot angle approach, foot region in contact and phase of gait cycle ultimately provides a more potent signal to the spinal cord and brain centres involved in motor skill learning, execution and regulation to carry out a task. Consequently, stimulating a stronger reaction to ground forces enables stronger and faster responses away from the ground, and more sensory signal input from the broader array of activated mechanoreceptors and proprioceptors together are integrated by the nervous system reflexes, spinal neural pathways and higher centres to permit more accurate processing of muscular responses and recruitment. This increased stimulation can ultimately lead to performance improvements as the body becomes accustomed to the new feelings provided by the insole 1 of the present invention.

The raised portions, formations and contours on the upper face 5 of the insole 1 are formed to mirror major sensitive regions of a user's plantar foot, in use, for example, such regions would include any or any combination of: the medial longitudinal arch, lateral longitudinal arch, anterior transverse arch, heel, fifth metatarsal and toe and/or first metatarsal and toe.

The thickness and/or density of the insole may also be varied to accommodate users of differing body masses. For example, users with an increased body mass may require an insole at the very least of a greater standard thickness in order to provide a cushioning effect which lasts an appropriate amount of time. This may also be solved by forming the insole of a material with a greater density than would be needed for a user of lesser body mass. The raised portions may be formed of the same material and density as the rest of the insole to enable a more streamlined manufacturing process—the insole may be cut from a single material and cut/shaped appropriately. In other, more tailored examples, the raised portions projections, formations and/or nodes may be provided having a different density to that of the remainder of the body of the insole 1 so as to accommodate the additional pressure these particular regions may come under. Generally, the insole 1 of the present invention is formed from a polymeric material, typically a lightweight polymer. Preferably, polyurethane is used, and the insole may be formed from injection-moulded polyurethane. In other embodiments of the invention, the insole 1 may be formed from compression moulding or 3D construction, or combinations thereof. The upper face 5 may also include a further surface layer (not shown) attached, bonded and/or adhered thereto. Typically, the further surface layer may be a textured or tactile layer, provided to improve grip for a user's foot on the surface of the insole 1.

The insole 1 may also include one or more side or rear walls, which may also be raised relative to the upper face 5 of the insole 1. The walls may be provided at or along the interior side 9, the exterior side 11, or the rear 13. The raised wall portions enable a user's foot to be located correctly and comfortably on the upper face of the insole apparatus, in use, however, these are distinct from the raised portions 7 which are provided to stimulate the cutaneous mechanoreceptors in the foot. In some examples, though, at least part of a raised side wall, for example, that located on an interior side 9 may extend inwardly of the insole 1 ultimately forming one of the raised portions 7.

In some examples of the present invention, the insole 1 may further include one or more implants, sensors and/or other electronics items (not shown) located within its body. Such implants and/or sensors may be provided to detect motion, activity, stimulation and/or the like of the user, in use, and in some examples, may be provided to form part of, or communicate with any or any combination of integrated wearable technologies, or artificially assisted or augmented motion technologies. The implants, sensors and/or other electronics items would preferably be located in each of the portions, formations, projections, nodes or domes provided in the specific insole 1 designed for the user.

Finally, the insole 1 as described may be formed to be provided as an insert for any item of footwear and be insertable in and removable therefrom. Such items of footwear may include a shoe, sandal, boot, sock, sports-related footwear, high-top boots, basketball shoes, ski boots and/or the like. In other examples of the present invention, the insole 1 may be formed to be integral with the particular item of footwear, for example, it may be embedded within a shoe, trainer, sock and/or the like. In items of footwear, for example high-tops, basketball boots, ski boots, socks etc where the item extends up beyond the ankle of the user, the present invention may include further portions or node structures on the footwear item, directed at, for example, lateral and medial ankle, and/or posterior region adjacent the tendoachilles region of a user. This may be provided as a one piece knitted, laminated, over moulded, injected &/or compression moulded item, or be formed from a combination of these techniques.

It is also envisaged by the present invention that there may be provided an item of footwear which includes an insole 1 as described herein, the insole being formed integrally with or be insertable in and removable from the item of footwear. In some embodiments, the item of footwear may be tailored specifically to receive the insole 1, thereby providing additional benefits to the user since the entire piece which is worn is designed to promote mechanoreceptor stimulation. For example, both the chassis and footbed of the item of footwear would be designed to receive the insole 1. In other examples, the item of footwear may be designed having an integral footbed contoured and with formations in the same manner as the insole 1.

Initial testing of the insole 1 and footwear of the present invention show significant improvements over conventional footwear. In one example, tests were undertaken to measure the increase in performance of golfers when striking the ball. The results show the average improvement between tests using an insole 1 according to the invention inserted into a regular golf shoe, and an insole 1 according to the present invention inserted into a shoe having a chassis designed specifically for receipt of the insole 1, versus use simply in a regular golf shoe:

Drive distance of ball increased an average of 10 metres using embodiments according to the present invention;
The ground or downward force was increased by an average of up to 12% versus use in a regular golf shoe;
Club head speed was increased by an average of 5 km/h using embodiments according to the present invention versus use in a regular golf shoe.

Further testing of the benefits of the present invention was carried out at Stadelhofen Zurich Kantonal Schule: an independent test was conducted to study if activated foot muscles can generate more speed for a human running 60 metres.

Group A—10 young adults called the "Control Group" wear their own running shoes.

Group B—10 young adults called the "Test Group" wear an embodiment of the present invention, branded "Tyfo Footbed 4s" inside their own running shoes.

Test 1 criteria as follows:
All 20 runners asked to sprint 60 metres.
Times for each runner taken and mean average times for each group calculated as follows:
Group A mean average time: 9.17 seconds;
Group B mean average time: 9.45 seconds.
All 20 athletes were then required to train at least 4 times a week for 6 weeks.
Test 2 criteria as follows:
All 20 runners asked to sprint 60 metres.
Times for each runner taken and mean average times for each group calculated as follows:
Group A mean average time: 8.96 seconds;
Group B mean average time: 8.77 seconds.

Group A was the faster group, as a whole, after Test 1, and after the 6-week training period, their times improved by an average of 0.21 seconds over the 60 metres, which shows that some training improved their speed.

Group B was the slower group, as a whole, after Test 1 (by 0.28 seconds), and after the 6-week training period, their times significantly improved by an average of 0.68 seconds over the 60 metres. The degree of improvement is not only substantially greater than that of Group A, but Group B in fact became the faster group, as a whole, after Test 2, by 0.19 seconds.

Group B showed a speed improvement 3 times greater than that of Group A.

In Test 1 Group A had more runners under 9 seconds for the 60 m sprint than Group B; however, in Test 2 Group B now achieved more runners under 9 seconds than Group A.

These initial results clearly illustrate the significant improvement in performance, caused by increased muscle stimulation in the foot, when using insoles and/or footwear according to the present invention, over and above that which is conventionally used at present. Whereas insoles provided for in the prior art merely provide raised cushioning pads as a means to provide increased comfort or stability, the present invention has been tested with positive results, and has shown that providing an insole with raised portions, projections, domes etc. of the right size, shape, hardness/density and in the right location can effectively penetrate the skin surface and open up the receptors in order to create constant messaging between the muscle and the brain. This subsequently increases proprioceptive connectivity allowing the muscle to grow in strength and awareness of contact and pressure.

The invention claimed is:

1. An insole apparatus for use with an item of footwear, said insole apparatus including:
   an upper face and an opposing lower face, said upper face arranged to interface with a sole of a user's foot when in use;
   wherein at least two or more regions of an upper surface of the upper face comprise at least one or more raised portions, said at least one or more regions of the upper surface are positioned to target and interface with at least two regions of cutaneous mechanoreceptors in the user's foot when in use,
   wherein said at least one or more raised portions of the insole apparatus includes a first raised dome having a maximum height at an apex of between 8 to 30 mm relative to a remainder of the upper face in the region of the upper face which targets a central forefoot of a user when in use, and a second raised dome having a maximum height at an apex of between 12 to 40 mm relative to a remainder of the upper face in the region of the upper face which targets a medial midfoot region of the user when in use,
   and a plurality of further raised portions which are located on the upper face of said insole apparatus configured to target any one or any combination of:
   medially at a base of the first metatarsal phalangeal joint;
   a base of a first interphalangeal joint closest to a midline and extending to a base of a second metatarsal phalangeal joint;
   a proximal base fifth metatarsal phalangeal joint;
   a central heel pad at a midline maximally posterior;
   at a heel pad at 50% of a heel length maximally laterally;
   a midline proximal limit of the heel pad; and
   medially on a medial midfoot portion; and wherein one or more of a raised side and/or a rear portion located at or along the periphery of the insole apparatus is configured to enable a user's foot to be located on the upper face of the insole apparatus relative to the raised portions when in use;

a plurality of smaller dimples or formations located across a remaining surface of the insole, and said plurality of smaller dimples or formations are designed to have a height which is less than the maximum height at the apices of the first and second domes of the at least one or more raised portions;

wherein a location and size of a distribution of the at least one or more raised portions versus the plurality of smaller dimples or formations is configured to target at least a combination of two or more fast adapting (FAI, FAII) and slow adapting (SAI, SAII) cutaneous mechanoreceptors in a user's foot in a non-uniform manner when in use; and wherein the upper face of the insole includes a further surface layer that is textured or tactile to improve grip on the surface of the insole.

2. The apparatus according to claim 1, wherein said at least one or more raised portions include any one or a combination of a plurality of formations, projections and/or nodes, or a single-shaped raised portion or formation across the at least one or more regions of the upper face.

3. The apparatus according to claim 1, wherein said at least one or more raised portions extend from a proximal one-third of a first metatarsal shaft base to one-third of a fourth metatarsal shaft base of the user's foot when in use.

4. The apparatus according to claim 1, wherein one of said at least two or more raised portions is located in a region of the insole apparatus from where a medial longitudinal arch borders, and from a heel region of the insole apparatus to a point mirroring a base of a first metatarsal phalangeal joint of the user when in use.

5. The apparatus according to claim 1, wherein the plurality of smaller dimples or formations are provided on the upper face across at least a part of the remaining region where there are at least one or more raised portions.

6. The apparatus according to claim 1, wherein the plurality of smaller dimples or formations are provided on at least a part of a surface of the at least one or more raised portions.

7. The apparatus according to claim 1, wherein said apparatus is formed of materials such that a density of the insole apparatus is varied in different regions of the insole apparatus.

8. The apparatus according to claim 1, wherein said insole apparatus includes one or more implants, sensors and/or other electronics items located therein, which are provided to detect motion, activity, stimulation and/or the like of the user when in use.

9. An item of footwear including the insole apparatus, or a chassis specifically adapted to receive the insole apparatus, as defined in claim 1.

* * * * *